United States Patent
Diamond

[11] Patent Number: 5,975,295
[45] Date of Patent: Nov. 2, 1999

[54] APPARATUS AND METHOD FOR ORGANIZING AND RECAPPING MEDICAL NEEDLES AND SYRINGES

[76] Inventor: Richard B. Diamond, 622 Goldenwest St., Huntington Beach, Calif. 92648

[21] Appl. No.: 08/961,348

[22] Filed: Oct. 30, 1997

[51] Int. Cl.$^6$ ................................................. B65D 83/10
[52] U.S. Cl. ................................................ 206/366; 206/486
[58] Field of Search .................................... 206/366, 365, 206/488, 489, 495, 370, 486; 211/60.1, 70.1, 72; 604/192

[56] References Cited

U.S. PATENT DOCUMENTS

| | | | |
|---|---|---|---|
| 2,435,994 | 2/1948 | Zukerman | 206/366 |
| 4,726,466 | 2/1988 | Cooper | 206/366 |
| 4,972,950 | 11/1990 | Shillington | 206/366 |
| 5,047,019 | 9/1991 | Sincock | 604/192 |
| 5,057,282 | 10/1991 | Linder | 422/104 |
| 5,190,169 | 3/1993 | Sincock | 211/60.1 |
| 5,245,117 | 9/1993 | Withers et al. | 588/249 |
| 5,291,997 | 3/1994 | He et al. | 206/370 |

*Primary Examiner*—Paul T. Sewell
*Assistant Examiner*—Nhan T. Lam
*Attorney, Agent, or Firm*—Stetina Brunda Garred & Brucker

[57] ABSTRACT

Method and apparatus for holding and selectively positioning medical needle and syringe assemblies. The device comprises the combination of a housing and a retainer insert interconnectible therewith. The retainer insert is provided with a plurality of retainer holes formed thereon for receiving and frictionally retaining a needle cap extensible through respective ones thereof. Each respective needle cap retained thereby is oriented such that when the needle portion of a needle/syringe assembly is placed therewithin, the assembly is maintained in fixed position. Following use, the contaminated needles are removed from the device and disposed of via conventional means while the needle caps remain frictionally retained within the retainer insert. In the preferred embodiment, the retainer holes formed on the retainer insert are arranged in a row-like fashion to organize use of multiple needle/syringe devices, and may further be formed to take any of a variety of shapes necessary to provide adequate frictional retention of a given needle cap.

10 Claims, 3 Drawing Sheets

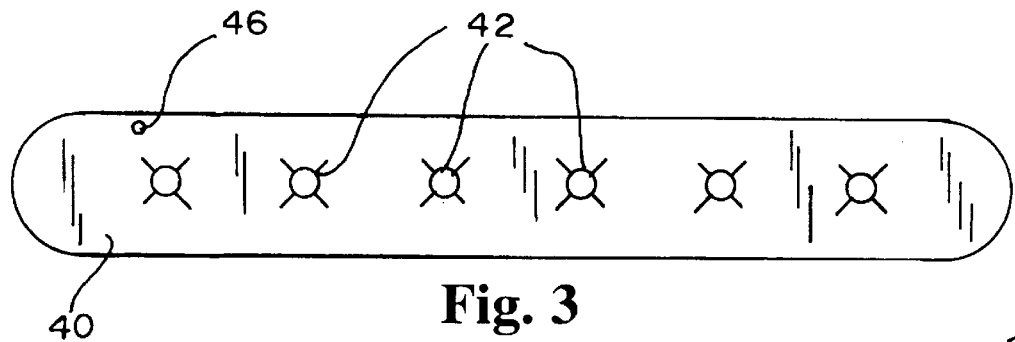
Fig. 3
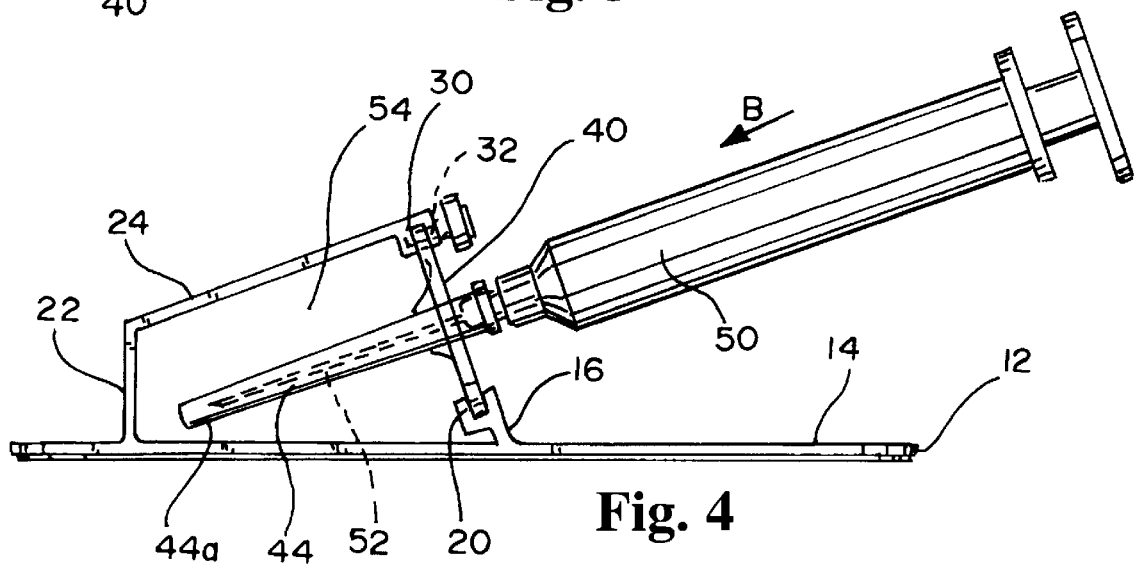
Fig. 4
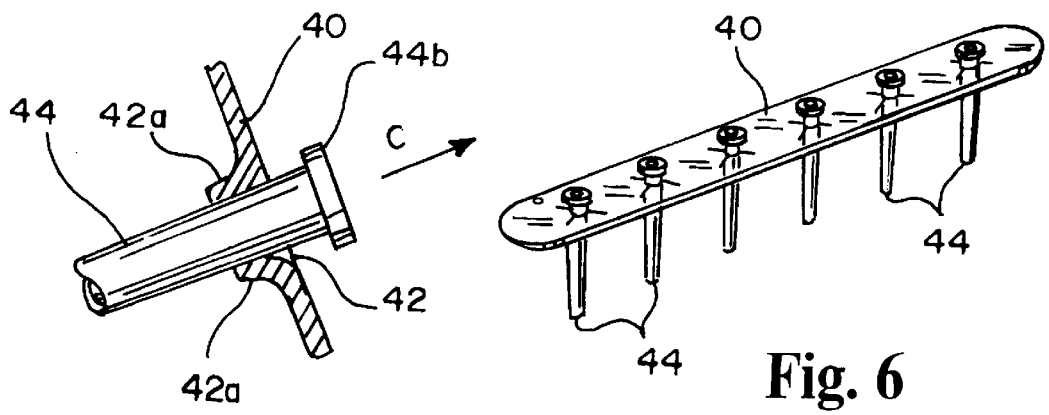
Fig. 5
Fig. 6 so,295

APPARATUS AND METHOD FOR ORGANIZING AND RECAPPING MEDICAL NEEDLES AND SYRINGES

FIELD OF THE INVENTION

The present invention relates generally to medical safety devices, and more particularly, to an apparatus and method for holding and selectively positioning medical needle and syringe assemblies.

BACKGROUND OF THE INVENTION

The use and handling of medical needle and syringe assemblies are well-known in the art. In this regard, such devices play a vital role in modern healthcare practice by virtue of their simple mechanical means for injecting or withdrawing fluids.

Despite their immense practicality, however, serious issues continue to exist with respect to the proper handling and disposal of such devices, and more particularly the needle or style portion thereof. As is well-known, once the needle has been exposed to bodily fluids there is thus created a substantial risk that such exposed needle portion will contain infective microbiological agents. More notably and commonly associated with these blood-borne diseases are AIDS and hepatitis B. which have the capability to infect an individual via an inadvertent needle-stick experience.

To minimize the risk of a needle-stick experience, capping devices, and in particular needle caps, are used in combination with needle and syringe assemblies to provide a protective covering over the needle portion thereof once the same has come into contact with bodily fluids. According to current practice, such capping devices are removed and subsequently replaced upon the exposed needle portion, often repeatedly, until the medical procedure is completed.

Following use of a given needle and syringe assembly, such needle portion, by virtue of its having come into contact with bodily fluids, must be disposed of through special handling procedures. Perhaps the most well-known and commonly utilized device to address the problem posed by the disposal of contaminated needles is referred to as the sharps container. Such device typically comprises a container having a port formed thereon into which a contaminated needle is inserted. A pair of scissors formed upon the container is designed and oriented to provide a cutting action across the portal entry to thus clip the needle portion off and thereafter safely house the same within the container.

While the sharps container and other similar devices are effective in removing and isolating contaminated needles and other contaminated sharps, substantial issues arise when attempting to separate and dispose of contaminated needles and other contaminated sharps from the capping devices with which they are used. In this regard, such capping devices must necessarily be utilized with such contaminated needles and sharps to provide a necessary protective covering over such contaminated sharps when the latter is not in use. As is well-recognized, such capping devices further the important goal of minimizing needle-stick experiences, and thus reduce the transmission of blood-borne diseases. However, the use of such capping devices with contaminated sharps has resulted in the concurrent disposal of both the capping device and the contaminated sharp, which are frequently disposed while interconnected to one another.

Recent changes in the law, however, have now prohibited the concurrent disposal of needles with needle caps while the same are interconnected. Indeed, strict fines and penalties are imposed for those healthcare providers and organizations that specifically fail to properly dispose of contaminated needles separate and apart from the caps used therewith. While systems have been developed, namely, needleless-type syringe systems, such systems are expensive and have not been well-received in the medical community. Additionally, such needless systems still necessarily employ the use of needles as is necessary to establish an intravenous connection.

In addition to the problems posed by proper isolation and disposal of contaminated needles and the capping devices used therewith has been the problem of organizing the use of multiple needle and syringe assemblies during a given medical procedure. In this respect, a wide variety of medical procedures often necessitate the use of multiple needle/syringe assemblies. For example, a variety of drugs may need to be administered throughout a given procedure. However, there currently does not exist any recognized apparatus or method for organizing the use of multiple needle/syringe assemblies. Rather, common practice typically comprises nothing more than arranging such needle/syringe assemblies upon a medical tray with the health care practitioner doing nothing more than grabbing the appropriate syringe assembly therefrom. Such technique, however, is exceptionally prone to disorganization and can actually increase the risk of a needle-stick experience insofar as improper orientation of such needle/syringe assemblies, and more particularly the needle portion thereof, can and often does come into close contact with the hands of the healthcare provider.

Accordingly, there is a need in the art for a method and apparatus for holding medical needles and syringes that enables the same to be used for a given procedure and thereafter provides means for substantially reducing the risk that the contaminated needle portion is disposed along with the cap with which it had been used. There is additionally a need in the art for a method and apparatus for holding medical needle and syringe assemblies that facilitates and provides means for organizing the use thereof during a given medical procedure. There is still further a need in the art for a method and apparatus for holding medical needle and syringe assemblies that is easy to use, may be easily and readily utilized with virtually all types of needle and syringe devices, is of simple construction, is space efficient, and inexpensive to manufacture.

SUMMARY OF THE INVENTION

The present invention specifically addresses and alleviates the aforementioned deficiencies in the art. Specifically, the present invention is directed to a method and apparatus for holding and positioning a plurality of needle and syringe assemblies during medical procedures. The apparatus comprises the combination of a housing and a retainer insert interconnectible therewith. The retainer insert, which is preferably fabricated from a rigid polymer material, includes a plurality of retainer holes which are die-cut therein. The retainer holes formed on the retainer insert are each sized and configured to receive and frictionally retain a needle cap extensible axially therethrough. The device is specifically designed and configured to retain the needle caps in a manner such that when the needle portion of a needle and syringe assembly is axially advanced into a respective one of the frictionally-retained needle caps, the assembly will assume a recapped configuration and be maintained in fixed position. Following use or contamination of a needle, such needle is disposed of by conventional means. The needle cap portion once used therewith, on the other hand, remains frictionally retained by the retainer hole formed on the retainer insert to thus ensure isolation and separate disposal of the needle caps from the needles.

In a preferred embodiment, the retainer insert is formed to be disposable. The housing may also be formed to be disposable or, alternatively, sterilizable for reuse. The housing and retainer insert are further preferably configured to interconnect with one another such that the plurality of needle caps held thereby are oriented such that the respective distal ends thereof are oriented toward the interior of the housing and the proximal portions thereof extending outwardly to thus enable easy access to the healthcare provider. Additionally, in a preferred embodiment the plurality of retainer holes formed upon the retainer insert are arranged in a row-like fashion to provide means for organizing the use of multiple needle and syringe devices, as may be required for a given medical procedure. Still further, the various retainer holes as formed upon the retainer insert may be specifically shaped and configured to engage with and frictionally retain any of a variety of given needle caps.

It is therefore an object of the present invention to provide a method and apparatus for holding a plurality of medical needle and syringe assemblies such that following the use thereof, the needle portion of such assembly will be in a condition to be disposed without having a needle cap affixed thereto.

Another object of the present invention is to provide a method and apparatus for holding medical needle and syringe assemblies that greatly facilitates the organization and use thereof during a medical procedure.

Another object of the present invention is to provide a method and apparatus for holding medical needle and syringe assemblies that may be easily and readily utilized with virtually all types of needles and syringes currently in use.

Another object of the present invention is to provide a method and apparatus f or holding medical needle and syringe assemblies that greatly facilitates the use of such needle/syringe assemblies while minimizing the risk of a needle-stick experience.

A still further object of the present invention is to provide a method and apparatus for holding medical needles and syringes that is of simple construction, easy and inexpensive to manufacture, is simple to use, and facilitates compliance with current safety guidelines regarding the disposal of contaminated needles and other contaminated sharps.

BRIEF DESCRIPTION OF THE DRAWINGS

These, as well as other features of the present invention, will become more apparent upon reference to the drawings, wherein:

FIG. 3 is a frontal view of the retainer insert component of the needle and syringe holding device of the present invention;

FIG. 4 is a side view of a needle/syringe assembly having a needle cap affixed thereto shown axially advanced into the needle and syringe holding device of the present invention;

FIG. 5 is a side view of a portion of a needle cap shown frictionally retained within a retainer hole formed on the retainer insert of the device of the present invention;

FIG. 6 is a perspective view of the retainer insert of the device of the present invention shown frictionally retaining a plurality of needle caps;

DETAILED DESCRIPTION OF THE PREFERRED EMBODIMENT

The detailed description set forth below in connection with the appended drawings is intended merely as a description of the presently preferred embodiment(s) of the invention, and is not intended to represent the only form(s) in which the present invention may be constructed or utilized. The description sets forth the functions and sequence of steps for construction and implementation of the invention in connection with the illustrated embodiments. It is to be understood, however, that the same or equivalent functions and sequences may be accomplished by different embodiments) that are also intended to be encompassed within the spirit and scope of the invention.

Figure 1:
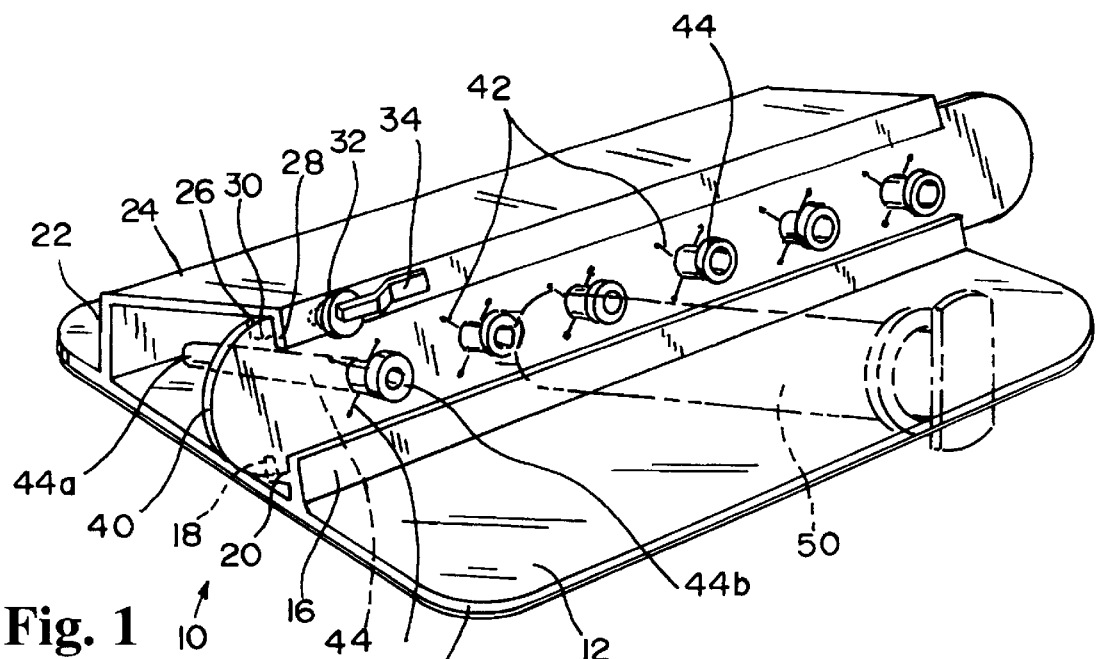
FIG. 1 is a perspective view of a needle and syringe holding device constructed in accordance with a preferred embodiment of the present invention, the device being shown retaining and selectively positioning a row of needle caps and one needle and syringe assembly, the latter shown in phantom.

Referring now to the Figures, and initially to FIG. 1, there is shown an apparatus 10 for holding and selectively positioning a plurality of medical needle and syringe assemblies, such as 50 shown in phantom. The apparatus 10 comprises the combination of a housing 12 and a retainer insert 40 interconnectible therewith. As illustrated, the housing 12 is provided with a base portion 14 upon which is formed a first upwardly extending sidewall 16, the latter having an arm 18 protruding rearwardly therefrom. Arm 18 and sidewall 16 cooperate to define a first notch or slot 20 that is designed and configured to mate with and hold a portion of the peripheral edge of retainer insert 40. Additionally formed on the base 14 of housing 12 is a second upwardly extending sidewall 22 from which extends a ceiling or cover 24. Formed at the distalmost end of ceiling 24 are depending flanges, 26 and 28 which, in combination with ceiling 24, define a second notch or slot 30, the latter also being designed and configured to mate with and hold a portion of the peripheral edge of retainer insert 40. The housing 12, and more particularly depending flange 28, has formed thereon an anchor 32, preferably having a lever 34, for releasably securing the retainer insert 40 to the housing 12.

Figure 2:
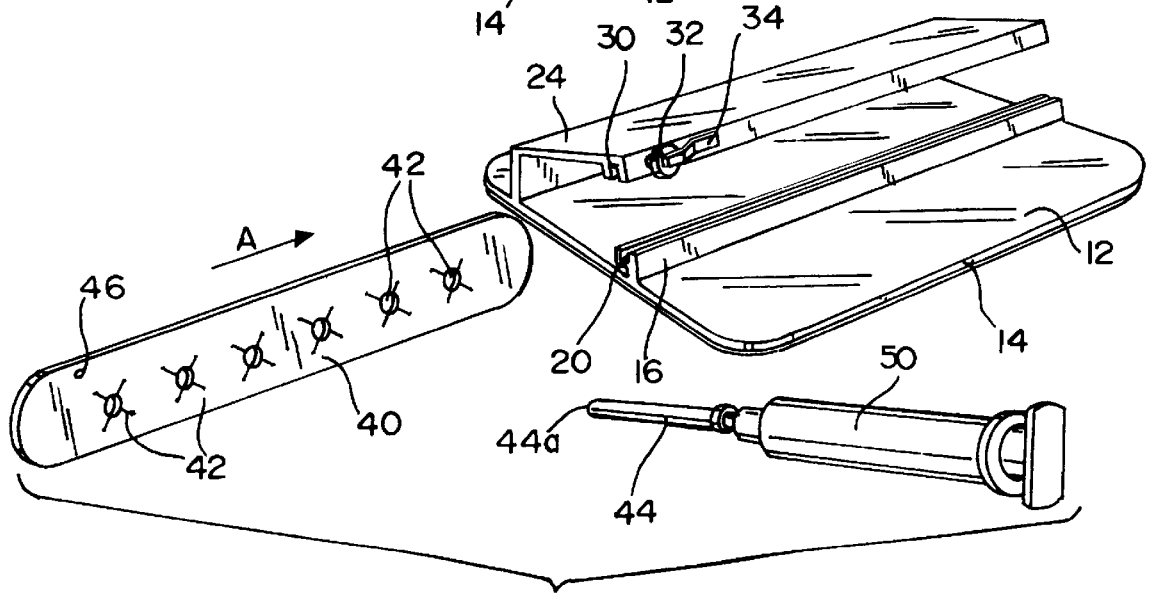
FIG. 2 is a perspective view of the components comprising the needle/syringe holding device of the present invention further perspectively illustrating a needle and syringe assembly having a needle cap affixed thereto.

As discussed above, retainer insert 40 is specifically designed and configured to interconnect with housing 12. In this regard, retainer insert 40, which is preferably fabricated from a rigid polymer material such as polyethylene and the like, is preferably formed to have a peripheral edge that may be received within notches 20 and 30 and securably held thereby. Formed upon the retainer insert 40 are a plurality of retainer holes 42, the latter preferably being arranged in a row-like fashion, as illustrated in FIG. 3. As discussed further below, such row-like arrangement of the retainer holes 42 facilitates and organizes the use of multiple needle/syringe devices during a given procedure. The retainer insert 40 further preferably includes a registry aperture 46 formed thereon for aligning and registering with anchor 32 formed on the housing. In this regard, and as shown in FIG. 2, the retainer insert 40 is simply and easily attached to the housing 12 by sliding the retainer insert 40 in the direction indicated by the letter A into upper and lower slots 20 and 30 so that portions of the peripheral edge of the retainer insert 40 become nested therewithin.

As best illustrated in FIGS. 1 and 4, the retainer insert 40, and more particularly the retainer holes 42 formed thereon, hold and maintain a plurality of needle caps 44 in a selectively fixed position such that the needle portion 52 of a needle and syringe assembly 50, as shown in FIG. 4, is maintained in a safely recapped configuration. The needle caps 44, as strategically held by the present invention, further positions such needle/syringe assemblies 50 such that the latter may be easily accessed and replaced within the selectively positioned needle caps 44 during their use. Additionally, by virtue of the row-like arrangement of the retainer holes 42 formed upon the retainer insert 40, there is further provided means for organizing the use of multiple needle/syringe assemblies So during a given medical procedure. As will be recognized by those skilled in the art, devices for organizing the use of multiple medical needle/syringe assemblies has been lacking in the prior art.

To achieve the desired positioning of the plurality of needle caps, and hence the needle and syringe assemblies to be held thereby, the retainer insert 40 and retainer holes 42 formed thereon are positioned by housing 12 such that when a respective cap 44 is axially extended through a given retainer hole 42, the distal end 44a of the cap 44 is angled downwardly into a chamber 54 defined by the base 14, sidewall 22 and ceiling 24 of the housing 12, as illustrated in FIG. 4. Advantageously, by positioning the needle caps 44 in such a manner, there is further minimized the risk of a needle-stick experience insofar as the needle portion 52 of the needle and syringe assembly 50 is selectively positioned and oriented away from the healthcare practitioner and into the chamber 54 formed on the housing 12, which thus provides additional shielding of the needle portion 52 from exposure when not in use.

As further illustrated in FIG. 4, each respective cap 44 becomes frictionally retained within a given retainer hole 42 by axially advancing the same therein in the direction indicated by the letter B. In this regard, each respective needle cap 44 may be retained within a a given retainer hole 42 by positioning the same about the needle 52 of a needle and syringe assembly when in a capped configuration. Due to the frictional engagement between the needle cap 44 and the respective retainer hole 42 within which it is inserted, the needle cap 44 thus becomes frictionally retained therein after the syringe and needle device is axially withdrawn, as indicated by the letter C in FIG. 5. As shown, the opening of the retainer hole 42, and more particularly flap portions 42a created thereby, cause the retainer insert 40 to radially compress about the barrel portion of the needle cap 44 with the proximal end thereof extending rearwardly therefrom.

As will be appreciated by those skilled in the art, the compressive force radially exerted about the barrel portion of the needle cap 44 will be substantially greater than the force that would be necessary to retract the needles cap 44 from the retainer hole 42 in which it is retained.

Once so nested within a given retainer hole 42, the cap 44 will be positioned in such a manner that a given needle/syringe assembly will be outwardly positioned for easy access to the healthcare provider. As discussed above, each retainer hole 42 will form a tight enough fit about a given needle cap 44 so that such needle cap 44 remains firmly in place, irrespective of the number of times and force by which a given needle/syringe assembly is placed therewithin and withdrawn therefrom. Accordingly, each of a plurality of needle/syringe assemblies may be positioned upon and withdrawn from respective ones of the needle caps 44 as the latter are retained and positioned by the device 10 of the present invention.

Once each retainer hole of each plurality of retainer holes has become occupied with a needle cap 44, as depicted in FIG. 6, the retainer insert 40, with needle caps 44 retained thereon, is removed from the housing 12 and disposed of as an integral piece. To disconnect the retainer insert 40 from the housing, the anchor 32 need only be axially withdrawn from aperture 46 to enable the retainer insert 40 to slide away from the housing to which it is attached. In an alternative embodiment, the retainer insert 40 and housing may be formed as an integral unit whereby the unit as a whole, along with needle caps retained thereby, being disposed of in its entirety.

Advantageously, the needle caps 44, by virtue of their firm retention upon the retainer insert 40, will remain separated from the medical needles 52 with which the caps 44 are used during a procedure. In this regard, the caps 44 will be so firmly imbedded within the retainer insert 40 that such caps 44 will not disengage to interconnect with a given medical needle and syringe assembly 50. Accordingly, there is thus facilitated the separation of the contaminated needle from the needle cap 44 used therewith so that each respective component may be disposed of separate and apart from one another.

To ensure that a given needle cap 44 remains sufficiently retained within a given retainer hole 46, it will be recognized by those skilled in the art that each of such retainer holes 42 may be selectively shaped and configured to provide the necessary frictional grasp about a given needle cap 44 such that the same remains in a fixed position therewithin as a given needle and syringe device is axially inserted and withdrawn therefrom. Additionally, each of the retainer holes 42 should be sized to accommodate differing sizes of needle caps so that any of a variety of needle caps, as well as the given needle/syringe assembly into which it is to be affixed may adequately retained and positioned thereby. In this respect, it will be recognized by those skilled in the art that such retainer holes 42 will be capable of providing adequate frictional retention to those needle caps 44 used in connection with, but not limited to, hypodermic needles, caudal needles, hemorrhoidal needles and spinal needles.

Figure 7:
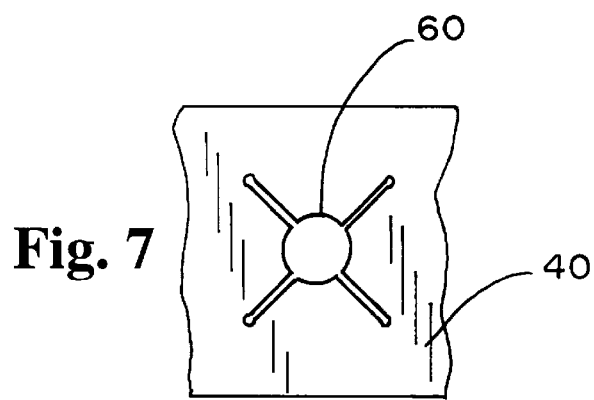
FIG. 7 is a frontal view of a first preferred retainer hole design formed upon the retainer insert component of the needle/syringe holding device of the present invention.
Figure 8A:
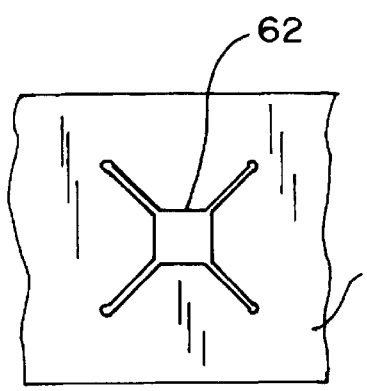
FIG. 8a is a frontal view of a second preferred retainer hole design formed upon the retainer insert component of the device of the present invention.
Figure 8B:
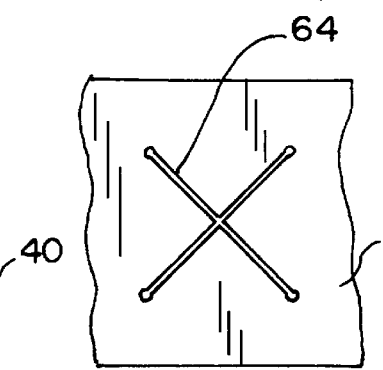
FIG. 8b is a frontal view of a third preferred retainer hole design formed upon the retainer insert component of the device of the present invention.
Figure 8C:
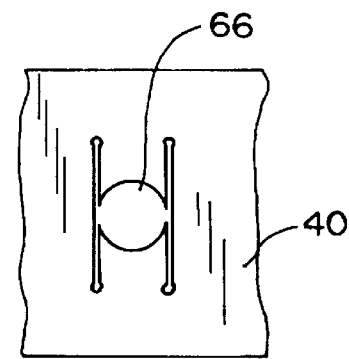
FIG. 8c is a frontal view of a fourth preferred retainer hole design formed upon the retainer insert component of the device of the present invention.
Figure 8D:
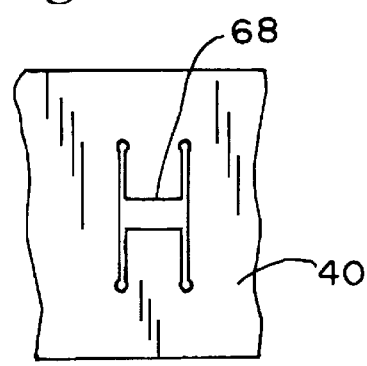
FIG. 8d is a frontal view of a fifth preferred retainer hole design formed upon the retainer insert component of the device of the present invention.
Figure 8E:
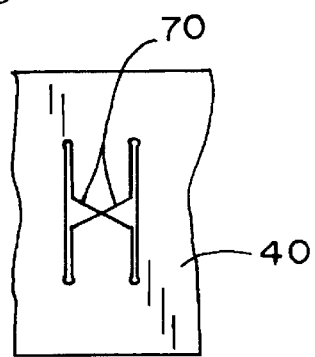
FIG. 8e is a frontal view of a sixth preferred retainer hole design formed upon the retainer insert component of the device of the present invention.

In a first preferred retainer hole design shown in FIG. 7, such retainer hole 60 comprises a generally circular configuration having four elongate slots emanating at right angles therefrom. Other preferred retainer hole designs, as illustrated in FIGS. 8a–8e, comprise a generally square-type retainer hole having elongate slots extending from the respective corners thereof, shown as 62 in FIG. 8a; an X-shaped retainer hole comprising two diagonally extending slots that intersect one another at right angles, shown as 64 in FIG. 8b; a generally circular aperture bordered on opposed sides thereof by two parallel-extending elongate slots, shown as 66 in FIG. 8c; and a central block portion having elongate slots formed on opposed sides thereof to form a generally H-shape aperture, shown as 68 in FIG. 8d. A still further preferred retainer hole design 70 is shown in FIG. 8e, which depicts the generally H-shape shown in FIG. 8d, but further having generally triangular portions formed as mirror images of one another formed in the general midportion thereof. As will be recognized, however, the retainer holes formed upon the retainer insert 40 of the present invention are not necessarily limited to the aforementioned designs, but rather may take any of a wide variety of shapes and configurations so long as there is provided the necessary frictional fit and retention of a given needle cap once the same has been extended axially therethrough.

With respect to the method of the present invention, such method comprises the steps of securably fastening a retainer insert having a plurality of apertures formed thereon to a housing member and axially inserting the distal end of a needle cap into a respective one of the apertures. The needle cap is held by the aperture formed on the retainer insert 40 in such a manner that the cap remains frictionally engaged therewithin and is held thereby with sufficient strength so as to support a needle/syringe assembly when the needle portion of such assembly is axially nested within the needle cap. The needle/syringe assembly may be removed and replaced from the frictionally retained needle cap as may be necessary for a given medical procedure. Once the needle portion of the needle/syringe assembly comes into contact with bodily fluid or otherwise becomes contaminated, such needle is then disposed of through conventional means. The needle cap remains frictionally retained upon the retainer insert 40 and is discarded therewith as a unit, separate and apart from the medical needles previously nested therewithin. Alternatively, the entire apparatus, namely, the housing 12 and the retainer insert 40 may be formed as an integral unit and thus may be disposed, with the needle caps retained therein, in its entirety.

Although the invention has been described herein with specific reference to a presently preferred embodiment thereof, it will be appreciated by those skilled in the art that various additions, modifications, deletions and alterations may be made to such preferred embodiment without departing from the spirit and scope of the invention. Accordingly, it is intended that all reasonably foreseeable additions, modifications, deletions and alterations be included within the scope of the invention as defined in the following claims.

What is claimed is:

1. An apparatus for holding and selectively positioning a medical needle and syringe assembly within a needle cap comprising:
    a) a housing defining an opening and having a fastener formed thereon;
    b) a retainer insert sheet positionable upon said housing and releasably attachable to said fastener such that said retainer insert sheet covers a portion of said opening, said retainer insert having at least one aperture formed thereon for securably capturing said needle cap when said needle cap is extended therethrough; and
    c) wherein said needle cap is so retained within said aperture of said retainer insert such that when said needle portion of said needle and syringe assembly is axially nested within said needle cap, said needle and syringe assembly is securably held and selectively positioned thereby.

2. The apparatus of claim 1 wherein said housing comprises a base having first and seconds upwardly extending sidewalls that cooperate to define sails opening, said first and second sidewalls having dedicated slots formed respectively thereon for receiving and interconnecting with a portion of the peripheral edge of said retainer insert, said first and second sidewalls being spaced relative one another to enable a portion of the distal end of said needle cap to extend therebetween when said needle cap is extended through said at least one aperture formed upon said retainer insert.

3. The apparatus of claim 2 wherein said first and second upwardly extending sidewalls are spaced relative one another such that said retainer insert assumes a slanted configuration when held thereby.

4. The apparatus of claim 1 wherein said housing is formed from a material suitable for autoclaving.

5. The apparatus of claim 1 wherein said base is formed from a disposable material.

6. The apparatus of claim 1 wherein said retainer insert includes a plurality of retaining holes formed thereon.

7. The apparatus of claim 6 wherein said plurality of retaining holes are arranged in a row-like fashion.

8. The apparatus of claim 1 wherein each respective one of said retaining holes is shaped and configured to frictionally retain a needle cap when said needle cap is extended axially therethrough.

9. The apparatus of claim 1 wherein said retainer insert is formed from a rigid polymer material.

10. The apparatus of claim 1 wherein said retainer insert is disposable.

* * * * *